(12) United States Patent
Hu et al.

(10) Patent No.: US 8,173,648 B2
(45) Date of Patent: May 8, 2012

(54) 1,2,3,4-TETRAHYDROISOQUINOLINE DERIVATIVES, PREPARATION PROCESS THEREFOR AND PHARMACEUTICAL COMPOSITION CONTAINING THE SAME

(75) Inventors: Ming-Kuan Hu, Taipei (TW); Yung-Feng Liao, Taipei (TW)

(73) Assignee: National Defense Medical Center, Taipei (TW)

( * ) Notice: Subject to any disclaimer, the term of this patent is extended or adjusted under 35 U.S.C. 154(b) by 864 days.

(21) Appl. No.: 12/174,563

(22) Filed: Jul. 16, 2008

(65) Prior Publication Data

US 2010/0016309 A1    Jan. 21, 2010

(51) Int. Cl.
*C07D 217/04* (2006.01)
*A61K 31/472* (2006.01)

(52) U.S. Cl. ............. 514/232.5; 546/150; 544/128; 514/307

(58) Field of Classification Search .......... None
See application file for complete search history.

(56) References Cited

U.S. PATENT DOCUMENTS 4,963,563 A * 10/1990 DeBernardis et al. ........ 514/307

OTHER PUBLICATIONS

Hu et al, Bioorganic & Medicinal Chemistry (2008), 16(4), pp. 1957-1965.*

* cited by examiner

*Primary Examiner* — Zinna Northington Davis
(74) *Attorney, Agent, or Firm* — Schmeiser, Olsen & Watts LLP

(57) ABSTRACT

The invention provides a type of novel 1,2,3,4-tetrahydroisoquinoline derivatives with a structure of formula (I):

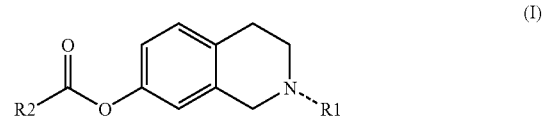

wherein R1 represents propargyl or cyclopropylmethyl; wherein R2 represents N-ethyl-N-methylamino, 1-Pyrrolidyl, 1-Piperidinyl, or 1-Morpholinyl. The invention provides further a process for preparing said derivatives and a pharmaceutical composition containing the same. Said derivatives can be used to modulate the proteolytic process of amyloid precursor proteins (APP), and provides further novel compounds useful for treating Alzheimer's disease (AD).

26 Claims, 4 Drawing Sheets

1,2,3,4-TETRAHYDROISOQUINOLINE DERIVATIVES, PREPARATION PROCESS THEREFOR AND PHARMACEUTICAL COMPOSITION CONTAINING THE SAME

BACKGROUND OF THE INVENTION

1. Field of the Invention

The invention relates to a type of novel 1,2,3,4-tetrahydroisoquinoline derivatives, and in particular, 1,2,3,4-tetrahydroisoquinoline derivatives useful for the treatment of Alzheimer's disease (AD), to processes for its preparation and pharmaceutical compositions containing the same.

2. Description of the Prior Art

Alzheimer's disease (AD) is a disease characterized in constant loss of nervous function due to death of brain nervous cells caused by deposition of non-hydrolytic toxic proteins in the brain. In 1906, Alois Alzheimer, a German neuropathologist, performed brain tissue dissection on a dead woman with serious dementia and had found some abnormal plaques and tangles of her nerve fibers in her brain tissue. In his study, it was found that these plaques consisted of non-soluble proteins and might result in inflammation and death of brain nerve cells. Alzheimer's disease was thus named after this pathologist's name.

Subjects of Alzheimer's disease primarily have nerve cells in brain cortex and hippocampus that have been damaged or died which result in gradual loss of their memory as well as dysfunctions in language and emotion. Incipient symptom is amnesia, daily behavior is marked by increasing loss of short-term memory, while long-term memory is comparatively not affected. Later stage symptoms consist of serious cognitive dysfunction, difficulty to adapt to social life, which result in problems of inability to understand conversation content, incapability to solve vital functions such as eating, drinking and the like, and finally, lead to paralysis. Alzheimer's disease itself is not lethal, and most such patients die due to accidents caused by dementia, long-term lying in bed, or other infections (e.g., septicemia, pneumonia, etc.) induced by reduction of immunity. The stages of Alzheimer's disease may last for about 1 to 25 years, and an AD patient may have an average life-span from diagnosis to death of about 8 to 10 years. Statistically, females are more likely to be affected than males, and prevalence rate of 11% occurs usually in population ages of more than 65 years old, and about 50% in more than 80 years old, and as such, it is also known as senile dementia.

One of the pathological characteristics of Alzheimer's disease is deposition of amyloid plaque in the brain. These plaques consist mainly of β amyloid-peptides (Aβ), β amyloid-peptides (Aβ) are not direct gene products, but products generated by various enzymatic cleavage of pre-formed amyloid precursor protein (APP). Amyloid precursor protein (APP) is a single transmembrane protein, and is associated with two degradation pathways: one of these comprising of producing soluble amyloid precursor protein α (sAPPα) by sequential cleavage with α-secretase and γ-secretase; the other pathway comprising of producing insoluble β amyloid-peptides (Aβ) by cleavage first with β-secretase followed with γ-secretase. In brain nerve cells of a patient with Alzheimer's disease, it is believed that the proteolytic process of amyloid precursor protein (APP) may pass mostly through a cleavage pathway with β-secretase and γ-secretase, and hence produce more insoluble βamyloid-peptides (Aβ). Since γ-secretase has various cleavage sites on amyloid precursor protein (APP), insoluble β amyloid-peptides (Aβ) of varying size may be produced. Among these Aβ, Aβ42 exhibits higher toxicity and tend to fibrillate into a polymer which deposit to form the core of a plaque and enable other types of β amyloid-peptides (Aβ) (mostly Aβ40) to deposit more easily over these plaques. At present it has been found that in brain of a patient of Alzheimer's disease, the proportion of Aβ42 in all Aβs is higher than that in a normal man.

From studies on cell level and in pharmacology, it has been found that γ-secretase is an aspartyl protease, and that, modulation with γ-secretase as the therapeutic target is considered to be a very important approach in the treatment of Alzheimer's disease. However, another approach for treatment of AD relates to the modulation on proteolytic process of α-secretase. Said proteolytic process comprises cleavage of amyloid precursor protein (APP) with α-secretase to produce soluble amyloid precursor protein α (sAPPα), which prevents indirectly the production of insoluble β amyloid-peptides (Aβ). In the present studies, it has been found that the proteolytic process of α-secretase may be modulated by mitogen-activated protein kinase (MAPK) pathway. MAPK pathway relates to a series of activation process for mitogen-activated protein kinase (MAPK) and extracellular signal-regulated protein kinase (ERK). Accordingly, how to modulate MAPK signaling cascade to influence further the proteolytic process of α-secretase constitutes a very important approach for the treatment of Alzheimer's disease.

Earlier development on medicament for treatment of Alzheimer's disease relied on symptom alleviation of Alzheimer's disease with drugs. The United States Food and Drug Administration (FDA) has approved four drugs for enhancing memory and retarding the progress of Alzheimer's disease. The first drug was the approved Tacrine (trade name: Cognex), which exhibited a number of side effects, including disadvantages of high hepato-toxicity, poor effect for enhancing memory and the like. Three other approved drugs were Donepezil (trade name: Aricept), Rivastigmine (trade name: Exelon), and galantamine (trade name: Reminyl), respectively. Said drugs had been proved to improve memory, and had little side effects. Among these, both of Tacrine and Donepezil inhibited degradation of acetylcholine by blocking the activity of cholinesterase. Both drugs could increase the content of acetylcholine in the brain so as to retard memory loss and help patients to perform daily life activities. These drugs could not cure Alzheimer's disease, but only mitigate symptom of Alzheimer's disease. In addition, these drugs were not effective for everyone, rather limited to be effective for early and immediate phase's patients of Alzheimer's disease. Therefore, it is still a medical bottleneck in the state of art for prevention and earlier diagnosis of Alzheimer's disease.

In view of the foregoing, the above-described approaches still have many disadvantages, and are not perfect designs and urgently need improvement.

The soluble form of APPα was found to possess potent neurotropic and neuroprotective activities against oxidative and excitotoxic insults. Further investigations indicated that rasagiline, a MAO-B inhibitor, and its carbamyl-containing derivative, TV-3326, regulate MEK-dependent APP processing in SH-SY5Y neuroblastoma and PC12 cells, which resulted in the stimulation of release of the neuroprotective sAPPα. Nevertheless, selegiline, a well-known selective MAO-B inhibitor for increasing the efficacy of levodopa therapy in the treatment of Parkinson's disease, also exerted neuroprotective effects in various preclinical models. These results suggested that a crucial role for MEK-dependent pathways may be involved in the enhancement of sAPPα release by selegiline and rasagiline. Taken together, the secretase-mediated proteolysis of APP can be subject to multiple levels of regulation by intracellular pathways and the ERK activation could play a pivotal role in shifting the APP processing to the α-secretase-initiated non-amyloidogenic pathway synergistically blocking γ-secretase-dependent Aβ production. Conversely, reduction of formidable Aβ production by interfering γ-secretase activity with enzyme-targeted inhibitors might shift the APP processing to the α-secretase-mediated pathways. Thus, control of Aβ production by direct or indirect modulation of γ-secretase activity on APP opens the approaches toward the treatment of Alzheimer's disease.

As such, in view of the above-described disadvantages derived from the conventional drugs used for Alzheimer's disease, the inventors had thought to improve and innovate, and finally, after studying intensively for many years, had developed 1,2,3,4-tetrahydroisoquinoline derivatives according to the invention, its preparation process and pharmaceutical composition containing the same.

SUMMARY OF THE INVENTION

One object of the invention is to provide a type of novel 1,2,3,4-tetrahydroisoquinoline derivatives, by modifying chemically 1,2,3,4-tetrahydroisoquinoline through chemical synthesis steps, and obtaining finally a type of novel 1,2,3,4-tetrahydroisoquinoline derivatives with structure represented by formula (I), wherein R1 and R2 are defined hereinafter.

Another object of the invention is to provide a process for preparing a type of novel 1,2,3,4-tetrahydroisoquinoline derivatives with structure represented by formula (I), wherein R1 and R2 are defined hereinafter.

Still another object of the invention is to provide a pharmaceutical composition containing a type of novel 1,2,3,4-tetrahydroisoquinoline derivatives, wherein said pharmaceutical composition comprises novel 1,2,3,4-tetrahydroisoquinoline derivatives with structure represented by formula (I), wherein R1 and R2 are defined hereinafter, and can be used to treating Alzheimer's disease.

It is known that some monoamine oxidase B (MAO-B) inhibitors, including: rasagiline, carbamyl-containing rasagiline derivatives TV-3326 and selegiline, can regulate amyloid precursor protein (APP) proteolytic process via ERK-related pathway and reduce further production of insoluble β amyloid-peptides (Aβ), as well as the activation of extracellular signal-regulated protein kinase (ERK) can modulate indirectly the secretion of soluble amyloid precursor protein α (sAPPα). As a result, these monoamine oxidase B (MAO-B) inhibitors may be used to treating Alzheimer's disease. These conventional monoamine oxidase B (MAO-B) inhibitors possesses partial chemical structure of propargylamine, and it has been found that said structure is very important for the activation of ERK signal, but is irrelevant with the inhibition of monoamine oxidase B (MAO-B) activity. Moreover, conventional acetylcholinesterase inhibitors can be used in treating Alzheimer's disease. Such acetylcholinesterase inhibitors generally contain carbamoyl.

In order to achieve the above-described objects of the invention, the inventors use commercially available 1,2,3,4-tetrahydroisoquinoline as the starting material (3), perform various modifications on functional groups with chemical synthetic reaction, to form a type of novel 1,2,3,4-tetrahydroisoquinoline derivatives. Through chemical steps (a) to (f), novel 1,2,3,4-tetrahydroisoquinoline derivatives 11a-d and 12a-d can be obtained, respectively, which are derivatives having structure formula (I) as shown in FIG. 1, wherein R1 and R2 are defined therein.

Specifically, the invention employs the chemical synthesis method described in example 1 to modify 1,2,3,4-tetrahydroisoquinoline into a chemical structure similar to monoamine oxidase B (MAO-B) inhibitor, as well as to acetylcholinesterase inhibitor (i.e., having carbamoyl), and furthermore, investigate the role that said derivatives might play in the activation of ERK and in the secretion of soluble amyloid precursor protein α (sAPPα). Since conventional pathway for activating ERK may concurrently inhibit indirectly the activity of γ-secretase, the invention examines further in example 2 whether said derivatives influence the activity of γ-secretase.

These features and advantages of the present invention will be fully understood and appreciated from the following detailed description of the accompanying Drawings.

DETAILED DESCRIPTION OF THE PREFERRED EMBODIMENT

Figure 1:
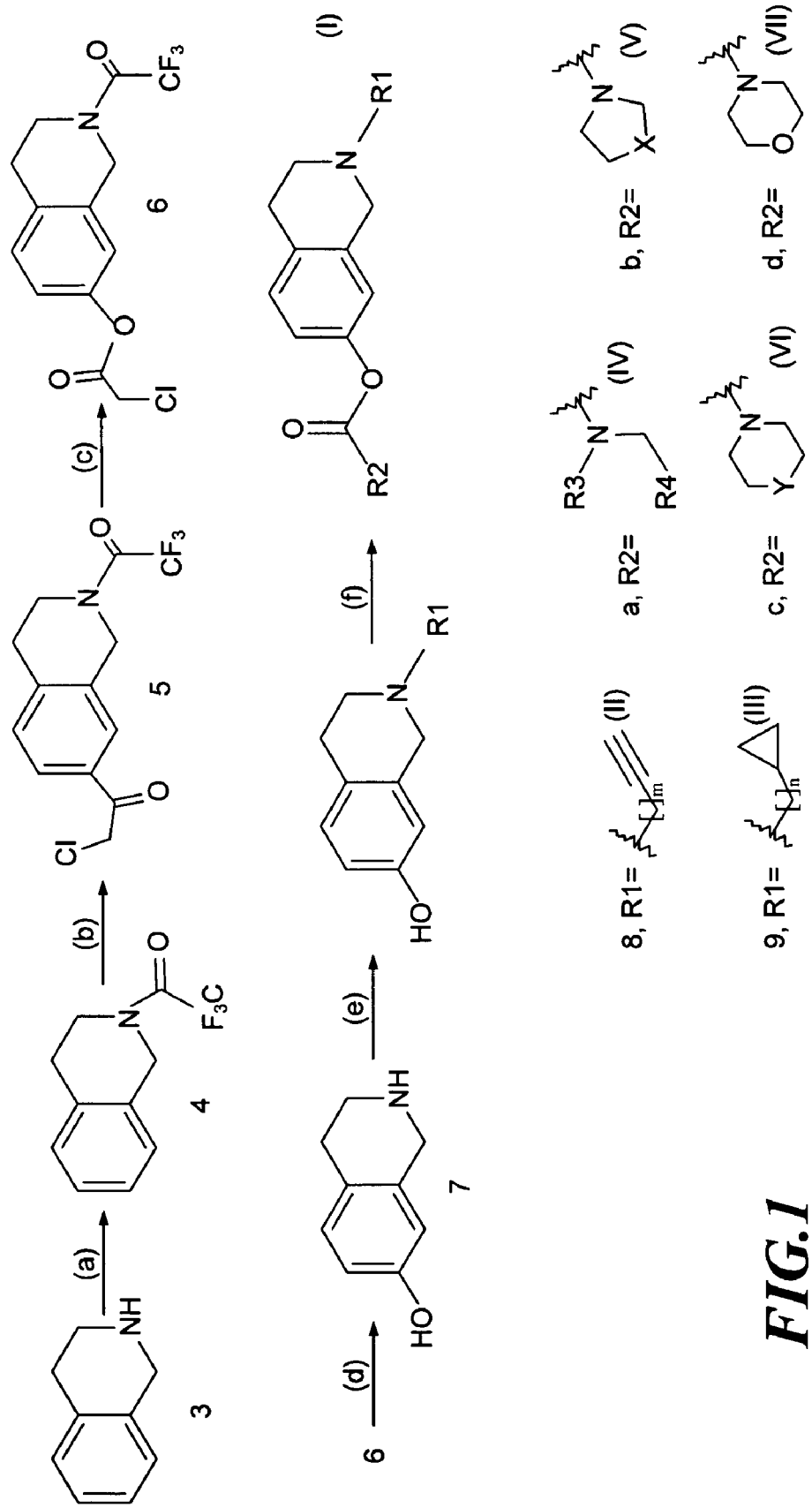
FIG. 1 is a flow chart showing a process for preparing 1,2,3,4-tetrahydroisoquinoline derivatives according to example 1.

The invention provides a type of novel 1,2,3,4-tetrahydroisoquinoline derivatives and pharmaceutical composition containing the same, wherein said derivatives and pharmaceutical composition containing the same comprise compound of formula (I), wherein R1 represents a structure of formula (II) showing in FIG. 1, m is 1, 2, 3 or 4; in a preferred embodiment, m is 1, R1 represents propargyl. Alternatively; R1 represents a structure of formula (II) showing in FIG. 1, n is 1, 2, 3 or 4; in a preferred embodiment, n is 1, R1 represents cyclopropylmethyl. Wherein R2 represents a structure of formula (IV) showing in FIG. 1, R3 represents a group selected from methyl (—CH$_3$), ethyl (CH$_2$CH$_3$) or propyl (—(CH$_2$)$_2$CH$_3$); R4 represents a group selected from methyl (—CH$_3$), ethyl (CH$_2$CH$_3$) or propyl (—(CH$_2$CH$_3$); in a preferred embodiment, R3 represents a methyl (—CH$_3$) and R4 represents a methyl (—CH$_3$), then R2 represent N-ethyl-N-methyl amino; or R2 represents a structure of formula (V) showing in FIG. 1, wherein X is selected from —CH$_2$—, oxygen or sulfur; in a preferred embodiment X is —CH$_2$—, then R2 represent 1-Pyrrolidyl: or R2 represents a structure of formula (VI), wherein Y is selected from —CH$_2$—, oxygen or sulfur; in a preferred embodiment Y is —CH$_2$—, then R2 represent 1-Piperidinyl; or R2 represent a structure of formula (VI), wherein Y is selected from —CH$_2$—, oxygen or sulfur; in a preferred embodiment, Y is oxygen, then R2 represents 1-Morpholinyl (structure of formula (VII) in FIG. 1); or pharmacologically acceptable salt form thereof, and appropriate pharmaceutically acceptable excipient or carrier.

Said pharmaceutical composition can be used to treat nerve cell necrosis, loss of memory and learning function, dementia and diseases involving impairment of cognitive process, caused by the increase of soluble amyloid-peptides β (Aβ), wherein diseases involving impairment of cognitive process include, but are not limited to, Alzheimer's disease or other dementia, or Parkinson's Disease.

The excipient that can be used in the invention comprises, but is not limited to, diluent, filler, binder, disintegrating agent, lubricant and the like. Further, said excipient include, but not limited to microcrystalline cellulose, polyvinylpyrrolidone (PVP), corn starch, modified starches, sodium carboxymethylstarch, resin, gelatinized starches, sugars, polyethylene glycol (PEG), polyvinyl alcohol hydroxypropyl cellulose, methyl cellulose, hydroxymethyl cellulose, hydroxypropyl methyl cellulose and the like.

The invention will be illustrated by way of following examples, without the intention that the invention is limited thereto.

Example 1

The Synthesis of 7-carbamoyl-1,2,3,4-tetrahydroisoquinoline Derivatives 11a-d and 12a-d As shown in FIG. 1, the invention used 1,2,3,4-tetrahydroisoquinoline as the reaction starting material (3) (available from US Sigma-Aldrich Co.), and carried out chemical synthetic reactions to modify various functional groups to produce novel derivatives with structure of formula (I).

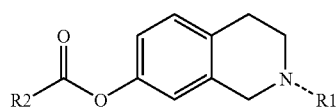

(I)

The chemical synthesis steps used to prepare said novel 1,2,3,4-tetrahydroisoquinoline derivatives will be described below:

Step (a): N-Trifluoroacetyl-1,2,3,4-tetrahydroisoquinoline (4)

To an ice-cooled solution of trifluoroacetic anhydride (9 ml) in $CH_2Cl_2$ (32.4 ml) was added dropwise a solution of 1,2,3,4-tetrahydroisoquinoline (8 ml, 60 mmol) in $CH_2Cl_2$ and stirred under ice-cooling for 3.5 h. A solution of KOH (4.74 g, 85 mmol) in water (72 ml) was then added, and the reaction mixture was stirred for further 2 hours at room temperature. The resulting mixture was extracted with $CH_2Cl_2$ and the organic layer was dried over $MgSO_4$. The residue was taken on a silica gel column (n-hexane/EtOAc=3:1 as eluents) to give a yellow oil (9.92 g, 72%) of the title compound (4); TLC $R_f$=0.58 (n-hexane/EtOAc=1:1). $^1$H NMR (300 MHz, $CDCl_3$) (NMR, Varian Gemini): δ 7.29-7.19 (m, 4H, Aryl Hs); 4.80 (s, 2H, Ph-$CH_2$—N); 3.91-3.86 (m, 2H, Ph-$CH_2$—$CH_2$—N); 3.00 (br s, 2H, Ph-$CH_2$—$CH_2$—N). Fast Atom Bombardment Mass Spectrometry (FABMS) m/z: 230 (M+1) ($C_{11}H_{10}NOF_3$).

Step (b): 7-Chloroacetyl-N-trifluoroacetyl-1,2,3,4-tetrahydroisoquinoline (5)

To a suspension of $AlCl_3$ (24.16 g) in $CH_2Cl_2$ (162 ml) was added chloroacetyl chloride (15 ml) dropwise at 0-5° C. under argon for 20 min and left to warm to room temperature. To this mixture was added compound (4) (9.29 g, 40 mmol) over a period of 30 min at room temperature. The resulting mixture was then stirred for an additional 3 hours and poured onto a mixture of ice-cold water (407 ml). The mixture was stirred for 5 min, and the layers were separated. The aqueous layer was extracted with $CH_2Cl_2$ (2×200 ml). The combined organic layers were washed with water (2×240 ml) and 5% aqueous $NaHCO_3$ (3×240 ml). The organic layer was dried and the solvent evaporated to give a white solid (5) (10.47 g, 88%). TLC $R_f$=0.4 (n-hexane/EtOAc=3:1). mp: 120-122° C. $^1$H NMR (300 MHz, $CDCl_3$) (NMR, Varian Gemini): δ 7.78 (q, J=4 Hz, 1H, Aryl H), 7.34-7.26 (m, 2H, Aryl Hs), 4.87 (s, 2H, Ph-$CH_2$—N), 4.67 (s, 2H, —$CH_2$—C=O), 3.95-3.87 (m, 2H, —$CH_2$—N), 3.06-3.01 (m, 2H, Ph-$CH_2$—)—. Fast Atom Bombardment Mass Spectrometry (FABMS) m/z: 306 (M+1) ($C_{13}H_{11}NO_2ClF_3$).

Step (c): 7-Chloroacetoxy-N-trifluoroacetyl-1,2,3,4-tetrahydroisoquinoline (6)

Compound (5) (8.4 g, 27 mmol) was dissolved in anhydrous $CH_2Cl_2$ (58 ml) and 3-chloroperoxybenzoic acid (mCPBA) (12.3 g) was added in one portion. The suspension was cooled to 0° C., and trifluoroacetic acid (2.0 ml) was added dropwise over 5-10 min. The reaction flask was protected from light, and the mixture was stirred for 3-5 days at room temperature, poured onto water (100 ml), and neutralized with ammonium hydroxide solution. The layers were separated, and the aqueous layer was extracted with $CH_2Cl_2$ (60 ml). After purification on a silica gel column (n-hexane/EtOAc=2:1) the title compound was obtained as a yellow oil (6) (4.24 g, 48%). TLC $R_f$=0.5 (n-hexane/EtOAc=3:1). $^1$H NMR (300 MHz, $CDCl_3$) (NMR, Varian Gemini): δ 7.20 (t, J=7 Hz, 1H, Aryl H), 7.01-6.93 (m, 2H, 2H, Aryl Ha), 4.75 (s, 2H, Ph-$CH_2$—N), 4.33 (s, 2H, CO—$CH_2$—), 3.90-3.82 (m, 2H, M—$CH_2$—), 2.97-2.92 (m, 2H, Ph-$CH_2$—). Fast Atom Bombardment Mass Spectrometry (FABMS) m/z: 322 (M+1) ($C_{13}H_{11}NO_3ClF_3$).

Step (d): 7-Hydroxy-1,2,3,4-tetrahydroisoquinoline hydrochloride salt (7)

To a solution of (6) (3.6 g, 11 mmol) in MeOH (100 ml) was added 15% of aqueous NaSMe (10 ml, 107 mmol) at 20° C., After 2 h, the mixture was acidified with 3 N HCl to pH 1. The resulting precipitate was collected as a white solid (7) (54%). $R_f$=0.2 (DCM/MeOH=5:1). $^1$H NMR (300 MHz, $D_2O$) (NMR, Varian Gemini): δ 7.15-7.00 (m, 3H, 2H, Aryl Hs), 4.22 (d, J=6 Hz, 2H, Ph-$CH_2$—N), 3.80-3.58 (m, 2H, Ph-$CH_2$—$CH_2$—$CH_2$—N), 2.65 (t, J=5.4 Hz, 2H, Ph-$CH_2$—N). Fast Atom Bombardment Mass Spectrometry (FABMS) m/z: 186 (M+1) ($C_9H_{11}NO.HCl$).

N-alkylation of 7-Hydroxy-1,2,3,4-tetrahydroisoquinoline hydrochloride salt (7) was carried out using propargyl bromide, with partial constituent structure of formula (II) as shown in FIG. 1; or with cyclopropylmethyl bromides, with partial constituent structure of formula (III) as shown in FIG. 1, respectively, in alkaline environment described in step (e), and obtained 7-Hydroxy-N-propargyl-1,2,3,4-tetrahydroisoquinoline (8) or 7-Hydroxy-N-cyclopropylmethyl-1,2,3,4-tetrahydroisoquinoline (9), respectively.

step (e-1): 7-Hydroxy-N-propargyl-1,2,3,4-tetrahydroisoquinoline (8)

To a stirred mixture of hydrochloride salt (7) (1.7 g, 11 mmol) and $K_2CO_3$ (3 g, 22 mmol) in $CH_3N$ (33 ml) was added a solution of 80% propargyl bromide (1.3 ml, 11 mmol). The reaction mixture was continued to stir at room temperature under nitrogen for 25 hours and filtered. The filtrate was washed with water and the aqueous layer was extracted with EtOAc (2×40 ml). The organic layer was dried over anhydrous $MgSO_4$, filtered, and concentrated in vacuo. The resulting residue was taken on a silica gel column (DCM/MeOH=9:1 as eluents) to give a brown solid (110 mg, 50%) of the title compound (8): $R_f$=0.4 (DCM/MeOH=9:1). mp: 82-83° C. $^1$H NMR (300 MHz, $CDCl_3$) (NMR, Varian Gemini): δ 6.91 (d, J=8.1 Hz, 1H, Aryl H), 6.60 (d, J=8.1 Hz, 1H, Aryl H), 6.38 (s, 1H, Aryl H), 3.69 (d, J=23 Hz, 2H, Ph-CH2-N), 3.51 (d, J=1.8 Hz, 2H, N—$CH_2$—C≡C—), 2.84 (t, J=4 Hz, 4H, Ph-$CH_2$—$CH_2$—N), 2.31 (t, J=2 Hz, 1H, C≡CH). Fast Atom Bombardment Mass Spectrometry (FABMS) m/z: 188 (M+1) ($C_{12}H_{13}NO$).

Step (e-2): 7-Hydroxy-N-cyclopropylmethyl-1,2,3,4-tetrahydroisoquinoline (9)

To a stirred mixture of hydrochloride salt 7 (0.9 g, 6 mmol) and potassium carbonate (2.0 g, 12 mmol) in $CH_3CN$ (18 ml) was added a solution of 96% (bromomethyl)cyclopropane (0.6 ml, 6.3 mmol). The reaction mixture was stirred at room temperature under nitrogen for 25 hours and filtered. The filtrate was washed with water and the aqueous layer was extracted with ethyl acetate (20 ml×2). The organic layer was dried over $MgSO_4$. The residue was taken on a silica gel column (DCM/methanol=9:1 as eluents) to give a yellow solid (0.37 g, 57%) of the title compound (9); TLC $R_f$=0.3 (DCM/MeOH=9:1). mp: 118-119° C. $^1$H NMR (300 MHz, $CDCl_3$) (NMR, Varian Gemini): δ 6.87 (d, J=8.1 Hz, 1H, Aryl H), 6.58 (dd, J=8.1 Hz, 2.1 Hz, 1H, Aryl H); 6.24 (d, J=2.1 Hz, 1H, Aryl H), 3.58 (s, 2H, Ph-$CH_2$—N), 2.87 (dd, J=5 Hz, 4H, Ph-$CH_2$—$CH_2$—N), 2.48 (d, J=7 Hz, 2H, N—$CH_2$); 1.13-1.10 (m, 1H); 0.61-0.57 (m, 2H), 0.21 (q, J=4.8 Hz, 2H). Fast Atom Bombardment Mass Spectrometry (FABMS) m/z: 204 (M+1) ($C_{13}H_{17}NO$).

Finally, 7-Hydroxy-N-propargyl-1,2,3,4-tetrahydroisoquinoline (8) and 7-Hydroxy-N-cyclopropylmethyl-1,2,3,4-tetrahydroisoquinoline (9), were added in a solution of N,N-dialkylcarbamyl chloride analogous compound (R2-CO—Cl) (10a-d) in $CH_3CN$, wherein R2 represents, respectively, N-Ethyl-N-methyl amino, 1-Pyrrolidyl, 1-Piperidinyl or 1-Morpholinyl; said R2 possesses a structure of formula (IV), (V), (VI) or (VII), respectively; as such, analogous compound (R2-CO—Cl) (10a-d) were N-ethyl-N-methyl-carbamoyl chloride (10a), pyrrolidine carbonyl chloride (10b), piperidinyl carbonyl chloride (10c) and morpholine carbonyl chloride (10d), respectively, and after step (f), obtained 1,2,3,4-tetrahydroisoquinoline derivatives 11a-d and 12a-d respectively. Above-mentioned N-ethyl-N-methyl-carbamoyl chloride (10a), pyrrolidine carbonyl chloride (10b), piperidine carbonyl chloride (10c) and morpholine carbonyl chloride (10d), were commercially unavailable, but could be synthesized via conventional method as described in reference (1), using a solution of phosgene in toluene to give 10a-d.

Step (f-1): General Procedure for the Preparation of 11a-d

To a stirred and ice-cooled solution of (8) (1.0 equiv) in $CH_3CN$ was added each of N,N-dialkylcarbamyl chloride (R2-CO—Cl) (10a-d), followed by dropwise addition of NaH (60% in mineral oil, 1.3 equiv.). The reaction mixture was stirred for 2 hours at room temperature under argon. After evaporation of the solvent in vacuo, water was added and extracted with EtOAc (3×). The organic layers were combined, dried over $MgSO_4$, and evaporated to dryness in vacuo. The residue was purified by column chromatography to afford title compound.

Step (f-2): General Procedure for the Preparation of 12a-d

To a stirred and ice-cooled solution of 9 (1.0 equiv.) in $CH_3CN$ was added each of N,N-dialkylcarbamyl chloride (R2-CO—Cl) (10a-d), followed by dropwise addition of NaH (60% in mineral oil, 1.3 equiv). The reaction mixture was stirred for 2 hours at room temperature under argon. After evaporation of the solvent in vacuo, water was added and extracted with EtOAc (3×). The organic layers were combined, dried over $MgSO_4$, and evaporated to dryness in vacuo. The residue was purified by column chromatography to afford title compound.

Step (f-1-1): 7-(N-Methyl-N-ethylcarbamoyloxy)-N-propargyl-1,2,3,4-tetrahydroisoquinoline (11a)

7-Hydroxy-N-propargyl-1,2,3,4-tetrahydroisoquinoline (8) was mixed homogeneously with N-ethyl-N-methyl-carbamoyl chloride (10a) and then carried out step (f-1). Purified on a silica gel column (EtOAc/n-hexane=2:1) gave propargyl- and N-Ethyl-N-methyl amino-containing 7-(N-Methyl-N-ethylcarbamoyloxy)-N-propargyl-1,2,3,4-tetrahydroisoquinoline (11a) (Yield 50%). $^1$H NMR (300 MHz, $CDCl_3$) (NMR, Varian Gemini): δ 7.08 (d, J=8 Hz, 1H, Aryl H), 6.88 (d, J=7 Hz, 1H, Aryl H); 6.80 (s, 1H, Aryl H), 3.76 (s, 2H, Ph-$CH_2$—N), 3.50 (d, J=2 Hz, 2H, N—$CH_2$—CCH), 3.42 (q, J=7 Hz, 2H, N—$CH_2$—$CH_3$), 3.04-2.81 (m, 7H, N—$CH_3$, Ph-$CH_2$—$CH_2$—N), 2.28-2.26 (m, 1H, C≡CH), 1.25-1.15 (m, 3H, N—$CH_2$—$CH_3$); IR (KBr): ν $cm^{-1}$=3300, 2923, 1715. Fast Atom Bombardment Mass Spectrometry (FABMS) m/z: 273 (M+1) ($C_{16}H_{20}N_2O_2$).

Step (f-1-2): 7-(1-Pyrrolidinecarbamoyloxy)-N-propargyl-1,2,3,4-tetrahydroisoquinoline (11b)

7-Hydroxy-N-propargyl-1,2,3,4-tetrahydroisoquinoline (8) was mixed homogeneously with pyrrolidine carbonyl chloride (10b) and then carried out step (f-1). Purified on a silica gel column (EtOAc/n-hexane=2:1) gave propargyl- and 1-Pyrrolidyl-containing 7-(1-Pyrrolidinecarbamoyloxy)-N-propargyl-1,2,3,4-tetrahydroisoquinoline (11b) (Yield 53%). $^1$H NMR (300 MHz, $CDCl_3$) (NMR, Varian Gemini): δ 7.08 (d, J=8 Hz, 1H, Aryl H), δ 6.91 (dd, J=8 Hz, 2 Hz, 1H, Aryl H), 6.83 (d, J=2 Hz, 1H, Aryl H), 3.81 (s, 2H, Ph-$CH_2$), 3.55-3.44 (m, 6H, 2 N—$CH_2$—CCH), 2.94-2.90 (m, 4H, N—$CH_2$—$CH_2$), 2.30 (t, J=3 Hz, 1H, C≡CH), 1.98-1.89 (m, 4H): IR (KBr): ν $cm^{-1}$=3375, 2951, 1715. Fast Atom Bombardment Mass Spectrometry (FABMS) m/z: 285 (M+1) ($C_{17}H_{20}N_2O_2$).

Step (f-1-3): 7-(1-Piperidinecarbamoyloxy)-N-propargyl-1,2,3,4-tetrahydroisoquinoline (11c)

7-Hydroxy-N-propargyl-1,2,3,4-tetrahydroisoquinoline (8) was mixed homogeneously with piperidine carbonyl chloride (10c) and carried out step (f-1). Purified on a silica gel column (EtOAc/n-hexane=2:1) gave propargyl- and 1-Piperidinyl-containing 7-(1-Piperidinecarbamoyloxy)-N-propargyl-1,2,3,4-tetrahydroisoquinoline (11c) (Yield 50%). mp: 72-73° C. $^1$H NMR (300 MHz, $CDCl_3$) (NMR, Varian Gemini): δ 7.08 (d, J=8 Hz, $^1$H, Aryl H), 6.87 (dd, J=8 Hz, 2

Hz, 1H, Aryl H), 6.80 (d, J=2 Hz, 1H, Aryl H), 3.77 (s, 2H, Ph-CH$_2$—N), 3.52 (t, J=15 Hz, 4H, N—CH$_2$—), 2.94-2.85 (m, 4H, Ph-CH$_2$—CH$_2$—N); 2.28 (t, J=2 Hz, 1H, C≡CH), 1.63 (s, 6H,); IR (KBr): ν cm$^{-1}$=3255, 2926, 1717. Fast Atom Bombardment Mass Spectrometry (FABMS) m/z: 299 (M+1) (C$_{18}$H$_{22}$N$_2$O$_2$).

Step (f-1-4): 7-(1-Morpholinecarbamoyloxy)-N-propargyl-1,2,3,4-tetrahydroisoquinoline (11d)

7-Hydroxy-N-propargyl-1,2,3,4-tetrahydroisoquinoline (8) was mixed homogeneously with morpholine carbonyl chloride (10d) and carried out step (f-1). Purified on a silica gel column (EtOAc/n-hexane=2:1) gave propargyl- and 1-Morpholinyl-containing 7-(1-Morpholinecarbamoyloxy)-N-propargyl-1,2,3,4-tetrahydroisoquinoline (11d) (Yield 82%). $^1$H NMR (300 MHz, CDCl$_3$) (NMR, Varian Gemini): δ 7.10 (d, J=8.4 Hz, 1H, Aryl H), 6.90 (dd, J=8.4 Hz, 2.4 Hz, 1H, Aryl H), 6.81 (d, J=2.4 Hz, 1H, Aryl H), 3.83-3.56 (m, 12H, 2-OCH$_2$CH$_2$N—, Ph-CH$_2$—N, N—CH$_2$—C≡CH), 2.96-2.92 (m, 4H, Ph-CH$_2$—CH$_2$—N), 2.32 (t, J=2.4 Hz, 1H, —C≡CH); IR (KBr): ν cm$^{-1}$=3232, 2951, 1706. Fast Atom Bombardment Mass Spectrometry (FABMS) m/z: 301 (M+1) (C$_{17}$H$_{20}$N$_2$O$_3$).

Step (f-2-1): 7-(N-Methyl-N-ethylcarbamoyloxy)-N-cyclopropylmethyl-1,2,3,4-tetrahydroisoquinoline (12a)

7-Hydroxy-N-cyclopropylmethyl-1,2,3,4-tetrahydroisoquinoline (9) was mixed homogeneously with N-ethyl-N-methyl-carbamoyl chloride (10a) and carried out step (f-2). Purified on a silica gel column (DCM/MeOH=10:1) gave cyclopropylmethyl- and N-Ethyl-N-methyl amino-containing 7-(N-Methyl-N-ethyl-carbamoyloxy)-N-cyclopropylmethyl-1,2,3,4-tetrahydroisoquinoline (12a) (Yield 50%). $^1$H NMR (300 MHz, CDCl$_3$) (NMR, Varian Gemini): δ 7.06 (d, J=8 Hz, 1H, Aryl H); 6.84 (s, 1H, Aryl H); 6.81 (s, 1H, Aryl H): 3.71 (s, 2H, Ph-CH$_2$—N); δ 3.44, 3.39 (dd, J=7 Hz, 2H, CH$_3$—N—CH$_2$CH$_3$); 3.03-2.75 (m, 7H, CH$_3$—N—CH$_2$—CH$_3$, Ph-CH$_2$—CH$_2$—N); 2.42 (d, J=6 Hz, 2H, N—CH$_2$); 1.24-1.17 (m, 3H, —CH$_3$); 1.14-0.94 (q, J=7 Hz, 1H); 0.58-0.52 (m, 2H); 0.19-0.14 (m, 2H); IR (KBr): ν cm$^{-1}$=2924, 1715. Fast Atom Bombardment Mass Spectrometry (FABMS) m/z: 289 (M+1) (C$_{17}$H$_{24}$N$_2$O$_2$).

Step (f-2-2): 7-(1-Pyrrolidinecarbamoyloxy)-N-cyclopropylmethyl-1,2,3,4-tetrahydroisoquinoline (12b)

7-Hydroxy-N-cyclopropylmethyl-1,2,3,4-tetrahydroisoquinoline (9) was mixed homogeneously with pyrrolidine carbonyl chloride (10b) and carried out step (f-2). Purified on a silica gel column (DCM/MeOH=20:1) gave cyclopropylmethyl- and 1-Pyrrolidyl-containing 7-(1-Pyrrolidinecarbamoyloxy)-N-cyclopropylmethyl-1,2,3,4-tetrahydroisoquinoline (12b) (Yield 50%). $^1$H NMR (300 MHz, CDCl$_3$) (NMR, Varian Gemini): δ 7.08 (d, J=8.1 Hz, 1H, Aryl H), 6.90 (d, J=8.1 Hz, 1H, Aryl H); δ 6.84 (s, 1H, Aryl H), 3.80 (s, 2H, Ph-CH$_2$—N), 3.54 (t, J=5.1 Hz, 2H, N—CH$_2$—), 3.46 (t, J=5.1 Hz, 2H, N—CH$_2$—), 2.92 (br s, 4H, Ph-CH$_2$—CH$_2$—N); δ 2.51 (d, J=4.8 Hz, 2H, N—CH$_2$—C≡C—): 1.92 (br s, 4H, —CH$_2$—CH$_2$—); δ 1.03 (br s, 1H): 0.58 (dd, J=6.3 Hz, 1.5 Hz, 2H), 0.20 (d, J=1.5 Hz, 2H); IR (KBr): ν cm$^{-1}$=2876, 1715. Fast Atom Bombardment Mass Spectrometry (FABMS) m/z: 301 (M+1)(C$_{18}$H$_{24}$N$_2$O$_2$).

Step (f-2-3): 7-(1-Piperidinecarbamoyloxy)-N-cyclopropylmethyl-1,2,3,4-tetrahydroisoquinoline (12c)

7-Hydroxy-N-cyclopropylmethyl-1,2,3,4-tetrahydroisoquinoline (9) was mixed homogeneously with piperidine carbonyl chloride (10c) and carried out step (f-2). Purified on a silica gel column (DCM/MeOH=32:1) gave cyclopropylmethyl- and 1-Piperidinyl-containing 7-(1-Piperidinecarbamoyloxy)-N-cyclopropylmethyl-1,2,3,4-tetrahydroisoquinoline (12c) (Yield 50%). $^1$H NMR (300 MHz, CDCl$_3$) (NMR, Varian Gemini): δ 7.06 (d, J=8.4 Hz, 1H, Aryl H); 6.86 (dd, J=8.4 Hz, 2.4 Hz, 1H, Aryl H), 6.80 (d, J=2.4 Hz, 1H, Aryl H), 3.71 (s, 2H, Ph-CH$_2$—N), 3.57 (br s, 2H, N—CH$_2$—), 3.50 (br s, 2H, N—CH$_2$—), 2.92-2.81 (m, 4H, Ph-CH$_2$—CH$_2$—N), 2.44 (d, J=6.9 Hz, 2H, N—CH$_2$), 1.62 (br s, 6H); 1.00-0.95 (m, 1H); 0.59-0.53 (m, 2H); 0.20-0.15 (m, 2H); IR (KBr): ν cm$^{-1}$=2924, 1717. Fast Atom Bombardment Mass Spectrometry (FABMS) m/z; 315 (M+1) (C$_{19}$H$_{26}$N$_2$O$_2$).

Step (f-2-4): 7-(1-Morpholinecarbamoyloxy)-N-cyclopropylmethyl-1,2,3,4-tetrahydroisoquinoline (12d)

7-Hydroxy-N-cyclopropylmethyl-1,2,3,4-tetrahydroisoquinoline (9) was mixed homogeneously with morpholine carbonyl chloride (10d) and carried out step (f-2). Purified on a silica gel column (DCM/MeOH=10:1) gave cyclopropylmethyl- and 1-Morpholinyl-containing 7-(1-Morpholinecarbamoyloxy)-N-cyclopropylmethyl-1,2,3,4-tetrahydroisoquinoline (12d) (Yield 51%). $^1$H NMR (300 MHz, CDCl$_3$) (NMR, Varian Gemini): δ 7.08 (d, J=8.2 Hz, 1H, Aryl H), 6.86 (d, J=8.2 Hz, 1H, Aryl H), 6.81 (s, 1H, Aryl H), 3.75-3.57 (m, 10H, O—(—CH$_2$—CH$_2$)$_2$—N—, Ph-CH$_2$—N), 2.90 (t, J=5.7 Hz, 4H, —CH$_2$—N), 2.80 (t, J=5.7 Hz, 4H, Ph-CH$_2$—), 2.42 (d, J=6.6 Hz, N—CH$_2$—), 0.98-0.92 (m, 1H), 0.59-0.53 (m, 2H), 0.19-0.15 (m, 2H); IR (KBr): ν cm$^{-1}$=2924, 1717. Fast Atom Bombardment Mass Spectrometry (FABMS) m/z: 317 (M+1)(C$_{18}$H$_{24}$N$_2$O$_3$).

Finally, through chemical steps (a) to (f), novel 1,2,3,4-tetrahydroisoquinoline derivatives 11a-d and 12a-d can be obtained, respectively, which are derivatives having structure formula (I), wherein R1 and R2 are defined therein.

Example 2

Analysis of the Inhibiting Ability of 1,2,3,4-tetrahydroisoquinoline Derivatives on γ-Secretase Since said derivatives had similar chemical structure to selegiline and rasagiline, in this example, assays were carried out to determine whether said derivatives exhibited the activity of inhibiting γ-secretase, and further the ability of modulating proteolytic process of amyloid precursor protein (APP). In this example, a quantitative cell-based assay described in reference (2) and (3) was employed to measure the activity of γ-secretase in T-20 cell line.

To measure the activity of γ-secretase, it was essential to produce first a stably transfected cell T-20 in this example according to the following steps:
1. Construction of C99-Gal4-VP16/TO (C99-GV/TO) Plasmid A construction method had been disclosed in reference (2). Briefly described below, since amyloid precursor protein (APP) could be cleavaged with α-secretase or β-secretase to form fragment C83 (C terminal of amyloid precursor protein, with 83 amino acids) or C99 (C terminal of amyloid precursor protein, with 99 amino acids), with which, after being cleavaged with γ-secretase, a fragment of amyloid precursor protein intracellular domain (AICD) was formed. By employing genetic recombination technique and using APP695-Gal4-VP16 (APP-GV) as the DNA template (a plasmid obtained from Dr. Mark Bothwell (University of Washington, Seattle, Wash.), wherein APP695 DNA fragment encoded a fragment of amyloid precursor protein (APP) with full length of 695 amino acids, Gal4 was an yeast transcription factor, and VP16 was a viral transcription activator, a polymerase chain reaction (PGR) was carried out using a specific primer described in reference (2) to obtain a DNA sequence fragment of C99-Gal4-VP16 (C99-GV). Then, said DNA fragment (C99-GV) was cloned in a vector pcDNA5/TO (Invitrogen) to produce a tetracycline-inducible construction plasmid C99-Gal4-VP16/TO (C99-GV/TO).

2. Construction of Gal4-Lue Plasmid

A construction method disclosed in reference (2) was utilized in this example, which was briefly described below. To construct a vector bearing luciferase useful in a stably transfected cell, the full DNA sequence of the open reading frame in the reporter gene, luciferase, of said plasmid was cloned together with its upstream Gal4 promoter binding sequence into a vector pBudCE4.1 (Invitrogen). Finally, the plasmid was digested with restriction enzymes to remove the DNA sequence of Cytomegalovirus (CMV) promoter from the plasmid pBudCE4.1 followed by self-ligation, a Gal4 promoter-driven luciferase reporter construct, Gal4-Luc, was thus yielded, which contained a screening marker for zeocin-resistance.

3. Cell Culture

T-REx293 cells were maintained in Dulbecco's modified Eagle's medium (DMEM) supplemented with 10% fetal bovine serum (PBS) and 5 μg/ml of blasticidin. T-REx293 cells were purchased from Invitrogen. Cells were incubated in a humidified incubator at 37° C. in 5% $CO_2$. T-REx293 cell line was modified from Human embryonic kidney cell line (HEK293).

4. Generation of Stably Transfected Cell Lines (T-20)

A process for generating stably transfected cell line disclosed in reference (2) was employed and was described briefly below. T-REx293 cells were grown in 10-cm dishes until 50% confluence as described above. On the day of transfection, the culture medium was replaced with 8 ml of DMEM containing 10% FBS. T-REx293 cells were transfected with equal amounts of C99-GV/TO (5 μg) and Gal4-Luc (5 μg) by FuGENE 6 transfection reagent (Roche Applied Science) according to the manufacturer's instructions. Transfected cells were cultured in DMEM supplemented with 10% FBS, 200 μg/ml of hygromycin, 250 μg/ml of zeocin, and 5 μg/ml of blasticidin (DMEM-HZB), and single colonies resistant to antibiotic selection were isolated individually using cloning cylinders. Each of independent cell lines was screened for the tetracycline-induced expression of C99-GV and corresponding luciferase signals that can be attenuated by γ-secretase inhibitors. Individually isolated cell lines were plated into 96-well microplates in DMEM-HZB containing 5 μg/ml of tetracycline in the presence or absence of 10 μM compound E (obtained kindly from Dr. Michael Wolfe, Brigham and Women's Hospital, Harvard Medical School), a potent γ-secretase inhibitor, for 24 hours. Cell lysis and the addition of reagents for luciferase assay were completed simultaneously using the Steady-Glo luciferase assay system (Promega) as described in the manufacturer's instructions. Luciferase signals were determined by a VictorLight microplate luminometer (PerkinElmer). The optimal cell line was the one exhibiting the highest tetracycline-induced luciferase signal that can be significantly suppressed by compound E down to the basal level comparable with the luciferase signal obtained in the absence of tetracycline induction. Based on this criterion, clone T-20 was selected and optimized for the cell-based γ-secretase assay.

5. Cell-Based γ-Secretase Assay

A quantitative cell-based γ-secretase assay in T-20 cell line described in reference (2) was employed to measure the activity of γ-secretase. In this example, said assay and cell line thereof was used to measure effect of 1,2,3,4-tetrahydroisoquinoline derivatives on the activity of γ-secretase.

T-20 cells were routinely maintained in DMEM supplemented with 10% FBS, 200 μg/ml of hygromycin, 5 μg/ml of blasticidin, and 250 μg/ml of zeocin (DMEM-HZB). The stably transfected T-20 cells were detached from culture dishes by trypsinization, washed with PBS, and resuspended in DMEM-HZB, followed by plating onto 96-well microplates ($2 \times 10^4$ cells/50 μl/well) and incubating at 37° C. for 24 hours. Preliminarily, compounds diluted in DMEM-HZB were added to a final concentration of 10 μM in the presence of tetracycline (1 μg/ml). Treatments were terminated after incubation at 37° C. for 24 hours by adding directly an equivalent volume of the Steady-Glo luciferase assay reagent (Promega), and measurements of luciferase signals from each well were performed immediately with the VictorLight microplate luminometer) (PerkinElmer). Triplicates of each compound treatment were assayed. Luciferase signal from the stable line without tetracycline induction and compound treatment was referred to as one-fold of activation. Parallel testing with a cell line constitutively expressing only the luciferase reporter gene (e.g., under control of a CMV promoter) was performed as a control. In this example, T-20 cell line treated with a medium containing 1% DMSO and 1 μg/ml of tetracycline was used as the control group: T-20 cell line treated with medium containing 1% DMSO was used a negative group; and further, T-20 cell lines treated, respectively, with mediums containing different compounds (10 μM), 1% DMSO and 1 μg/ml of tetracycline were used as test groups for different compounds.

Briefly, T-20 cell line was induced by tetracycline to express C99-GV protein fragment on cell membrane. After cleavage of C99-GV fragment with γ-secretase, an ACID-GV fragment was released from cell membrane, and bound with Gal4 promoter binding domain to drive the expression of luciferase; conversely, if the activity of γ-secretase was inhibited by an inhibitor, the expression level of luciferase might lower or did not express at all.

6. Statistical Analysis

The data were presented as means±SD and triplicates of each compound treatment were measured in the experiments. The effects of the various synthesized compounds on the biological outcome were statistically examined using a one-way analysis of variance. Dunnets's test was used to compare individual compounds. In all cases, P<0.05 was accepted to denote significance.

7. Result

Figure 2:
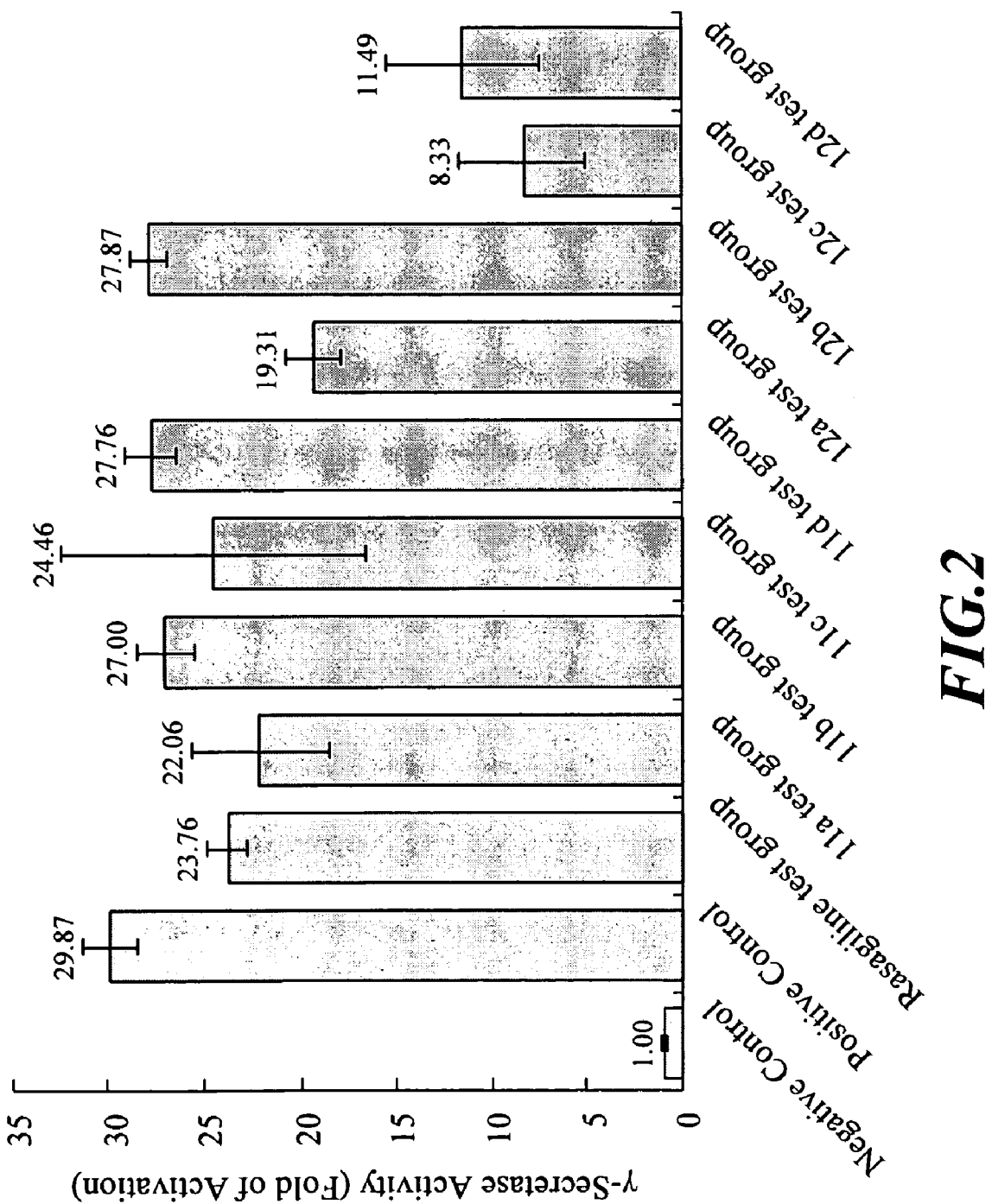
FIG. 2 shows the analytical results for the inhibition on the activity of γ-secretase with 1,2,3,4-tetrahydroisoquinoline derivatives according to example 2.

As shown in FIG. 2, when three test groups of 12a, c, d at concentration of 10 μM were compared with positive control group, 10 μM of 12a, c, d could inhibit the activity of γ-secretase up to about 35-72%. While test groups with rasagiline and other 1,2,3,4-tetrahydroisoquinoline derivatives were compared with positive control group, the activities of γ-secretase were lowered by about 6-15%. Accordingly, it was thus proved that 1,2,3,4-tetrahydroisoquinoline derivatives with structure of formula (I) (wherein R1 and R2 were defined therein) could inhibit the activity of γ-secretase.

Example 3

Cytotoxicity Assay of 1,2,3,4-tetrahydroisoquinoline Derivatives

In this example, animal cell was used to assay whether 1,2,3,4-tetrahydroisoquinoline derivatives exhibited cytotoxicity against cells. Animal cells used here included, but not limited to, Human embryonic kidney cells (HEK293) and other animal cells that were suitable for testing cytotoxicity.

In a preferred embodiment, said animal cell was human embryonic kidney cells (HEK293), which was used to test whether 1,2,3,4-tetrahydroisoquinoline derivatives exhibited cytotoxicity to said cell.

1. Cell Culture

Human embryonic kidney cells (HEK293) were maintained in Dulbecco's modified Eagle's medium (DMEM) supplemented with 10% fetal bovine serum (FBS) and each of 0.1 mg/ml of penicillin and streptomycin. HEK293 cells were purchased from Invitrogen. T-20 was the subclonal cell line of HEK293 and γ-30 was one disclosed in reference (3). Cells were incubated in a humidified incubator at 37° C. in 5% $CO_2$.

2. Cell Viability Assay.

The CellTiter 96® Aqueous Non-Radioactive Cell Proliferation Assay (Promega) is a colorimetric method for determining the number of viable cells in proliferation or chemosensitivity assays. The CellTiter 96® AQueous Assay is consisted of solutions of a novel tetrazolium compound (3-(4,5-dimethyl thiazol-2-yl)-5-(3-carboxymethoxyphenyl)-2-(4-sulfophenyl)-2H-tetrazolium, inner salt: MTS) and an electron coupling reagent (phenazine methosulfate: PMS). MTS is bioreduced by cells into a formazan product that is soluble in tissue culture medium. The absorbance of the formazan at 490 nm can be measured directly from 96-well assay plates without additional processing. The conversion of MTS into aqueous, soluble formazan is accomplished by dehydrogenase enzymes found in metabolically active cells. The quantity of formazan product as measured by the amount of 490 nm absorbance is directly proportional to the number of living cells in culture.

T-20 cells ($5 \times 10^4$/100 μl/well) were seeded onto wells of 96-well microplates in culture medium containing 10 μM of respective compounds (11a-d, 12a-d) and incubated at 37° C. for 24 hours. Viable cells were determined using the CellTiter 96® Aqueous Non-Radioactive Cell Proliferation Assay (Promega) as specified in the manufacturer's instructions. Briefly, following the addition of the combined MTS/PMS solution (20 μl/well), microplates were incubated for 3 hours at 37° C. The conversion of MTS into formazan in viable cells was quantified by the absorbance at 490 nm using a Synergy HT ELISA plate reader (BioTek). The number of living cells in culture was directly proportional to the absorbance at 490 nm. Viable cells in culture medium containing vehicle alone (1% DMSO) were referred to as 100% viability. The background absorbance shown at 0 cell/well was subtracted from these data.

In this example, T-20 cell line treated with medium containing 1% DMSO and 1 μg/ml of tetracycline was used as positive control group. T-20 cell line treated with medium containing 1% DMSO was used as the negative control group. T-20 cell lines treated with medium containing different compounds (10 μM), 1% DMSO and 1 μg/ml of tetracycline were used as test groups for different compounds, respectively.

3. Statistical Analysis

The statistical analysis in this example was same as described in example 2.

4. Result

Figure 3:
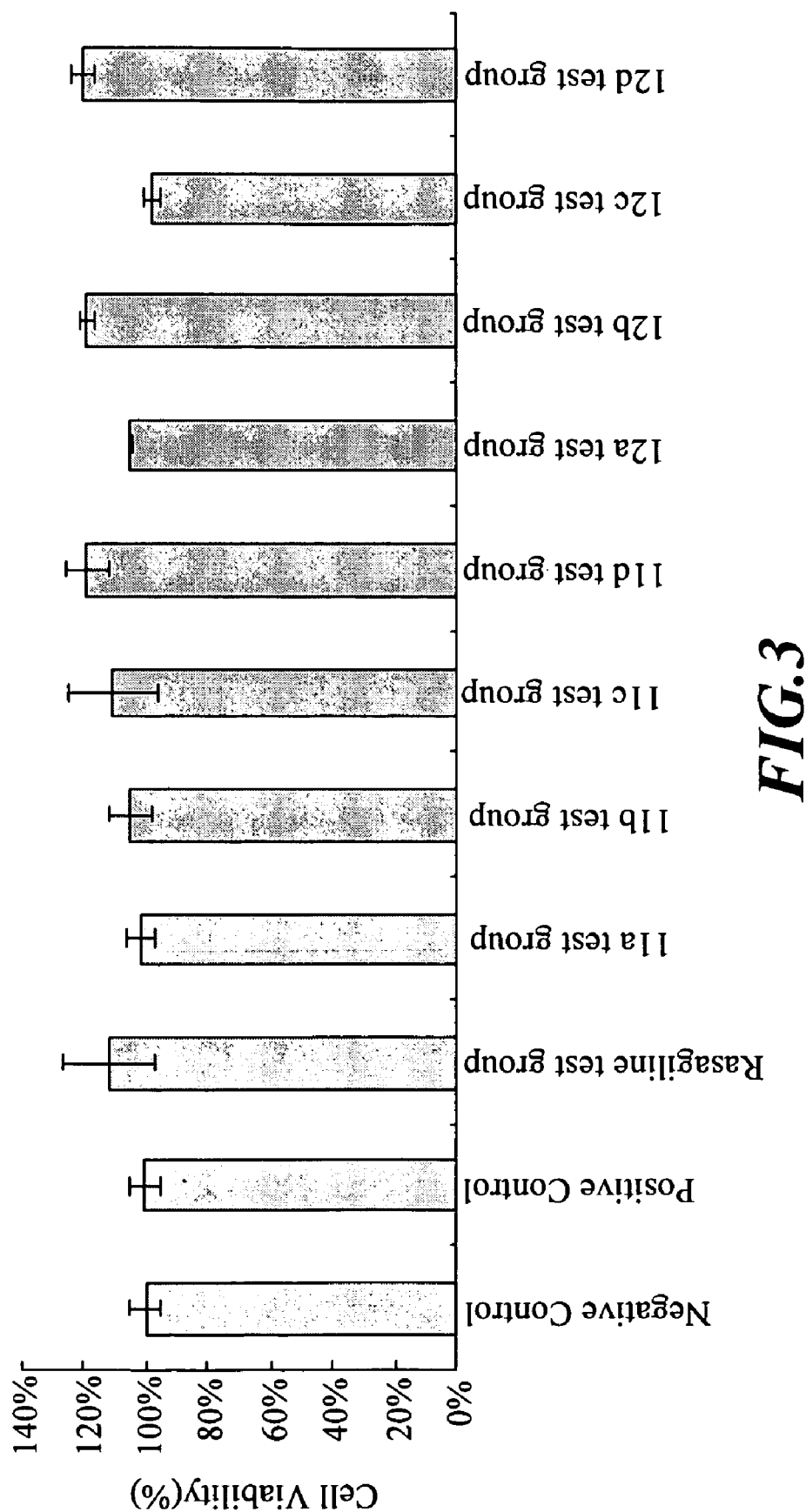
FIG. 3 shows the results from cytotoxicity assay with 1,2,3,4-tetrahydroisoquinoline derivatives according to example 3.

As shown in FIG. 3, the subclonal cell line T-20 of human embryonic kidney cell line (HEK293), when treated in every derivatives test group, had their cell viability compared with positive control group, negative control group, and rasagiline test group, demonstrated no significant difference, and hence revealed that 1,2,3,4-tetrahydroisoquinoline derivatives with structure of formula (I) (wherein R1 and R2 were defined therein) gave no significant cytotoxicity to human embryonic kidney cell line (HEK293).

Example 4

Analysis of the Inhibitory Ability of 1,2,3,4-tetrahydroisoquinoline Derivatives against Monoamine Oxidase B (MAO-B)

As indicated in reference (4), some monoamine oxidase B (MAO-B) inhibitors including: rasagiline, carbamyl-containing derivatives of rasagiline TV-3326 and selegiline, can regulate proteolytic process of amyloid precursor protein (APP) via ERK-related pathway, modulate indirectly the secretion of soluble amyloid precursor protein α (sAPPα), and thus reduce indirectly the production of insoluble β amyloid-peptides (Aβ). Therefore, these monoamine oxidase B (MAO-B) inhibitor might be used in the treatment of Alzheimer's disease. These monoamine oxidase B (MAO-B) inhibitors have partial constituent structure of propargylamine, and it has been found in reference (5) that such a structure was essential to the activation of ERK signal, but was irrelevant with the inhibition of the activity of monoamine oxidase B (MAO-B), accordingly, in the invention, chemical synthesis steps described in example 1 was used to modify 1,2,3,4-tetrahydroisoquinoline into a chemical structure similar to that in selegiline or rasagiline, as well as similar to carbamoyl chemical structure in acetylcholinesterase inhibitor, and furthermore, derivatives (11a-d and 12a-d) with similar structure to that in monoamine oxidase B (MAO-B) inhibitor were examined to determine their possible role against amyloid precursor protein proteolytic process.

At first, monoamine oxidase B (MAO-B) was purified from rat brain cortex, and then activity inhibition assay of these derivatives against monoamine oxidase B(MAO-B) was carried out.

1. Fluorometric Assay of Rat Brain Protein Content.

MAO-B enzyme preparations were prepared from brain cortex of decapitalized male F344/N rats. The brain cortex in PBS solution was frozen with liquid nitrogen and kept at −80° C. for 3 days. The homogenate was then obtained by centrifugation (14,000 rpm, 10 min) of the frontal cortex in 0.1 M potassium phosphate buffer (pH 7.4) at 4° C. and the supernatant was taken as the enzyme source for MAO. A standard solution containing 0.1 M potassium phosphate buffer and albumin were prepared in different concentration grades. Ten microliters of each solution was taken and added with 200 μl of BCA kit. Following the similar method, the above supernatant from brain cortex was diluted and 10 μl of stock solution taken and added with 2.00 μl of BCA kit. Both standard and sample solutions were incubated at 37° C. for 30 min. 200 μl of the solutions was added to each well of a 96-well microplate and the protein contents were measured with a fluorescence microplate reader by determining optical density at 595 nm.

2. MAO-B Inhibitory Assays.

To the supernatant (protein content, 80 µg/ml) in 96-well microplate was added with 1 U/ml HRP (Horseradish Peroxidase), 1 nM benzylamine, and 50 µM Amplex red in 0.1 M potassium phosphate buffer followed by the tested sample, which was prepared in 200 µg/ml in DMSO as stock solution. These mixtures were incubated at room temperature for 60 min and optical density was determined by a fluorometric reader. Its $IC_{50}$ was calculated then with the following formula. $IC_{50}$: median inhibitory concentration, which is defined in this example as the concentration of a inhibitor that is needed for inhibiting 50% activity of an enzyme.

Inhibition (%)=1−[($OD_{595}$ of sample/protein−$OD_{593}$ of sample)/$OD_{595}$ of blank]×100%

$OD_{595}$: Optical density at 595 nm (wavelength)
protein: protein content of control 3. Statistical Analysis The statistical analysis in this example was same as described in example 2.

TABLE 1

MAO-B inhibitory activity and log P values of tetrahydroisoquinoline derivatives 11a-d and 12a-d

| Compound | R2 | $IC_{50}$ (µM) | log P[a] |
|---|---|---|---|
| Rasagiline | | 2.1 ± 0.6 | 2.295 |
| 11a | N-Ethyl-N-methyl amino | 21.5 ± 1.0 | 2.252 |
| 11b | 1-Pyrrolidyl | 13.9 ± 0.5 | 2.235 |
| 11c | 1-Piperidinyl | 15.7 ± 2.2 | 2.632 |
| 11d | 1-Morpholinyl | 18.7 ± 1.6 | 1.567 |
| 12a | N-Ethyl-N-methyl amino | 12.8 ± 2.0 | 2.688 |
| 12b | 1-Pyrrolidyl | 14.9 ± 1.1 | 2.671 |
| 12c | 1-Piperidinyl | 11.6 ± 0.7 | 3.088 |
| 12d | 1-Morpholinyl | 18.5 ± 0.8 | 2.033 |

[a]Estimated lipophilicity by CAChe v. 6.1.

4. Result

As shown in the above table 1, although the inhibitory ability of 1,2,3,4-tetrahydroisoquinoline derivatives (11a-d) was less than that of rasagiline, at $IC_{50}$ of 10-20 µM, said derivatives (11a-d) could inhibit 50% of the activity of monoamine oxidase B (MAO-B). However, when 1,2,3,4-tetrahydroisoquinoline derivatives (12a-d) obtained by replacing the propargyl of 1,2,3,4-tetrahydroisoquinoline derivatives (11a-d) with cyclopropylmethyl were subjected to monoamine oxidase B (MAO-B) activity inhibitory assay, it could be found that the abilities to inhibit monoamine oxidase B (MAO-B) from each of 12a-d derivatives were similar to that from 11a-d. Meanwhile, lipophilicity calculated via CAChe v. 6.1 software indicated that derivatives 12a-d and 11a-d had similar size and lipophilicity (increased log P value of about 0.45), which facilitates the preparation of a drug (log P value of ordinary drug was about 2-5). Accordingly, it was demonstrated that 1,2,3,4-tetrahydroisoquinoline derivatives with structure of formula (I) (wherein R1 and R2 was defined therein) could be used to inhibit the activity of monoamine oxidase B (MAO-B).

Example 5

Assay for Extracellular Signal-Regulated Kinase (ERK) Activity

It was known that rasagiline or selegiline could be used to modulate the activation of ERK-related pathway, and the activation of that pathway can modulate α-secretase in direct or indirect manner, which can modulate further amyloid precursor protein (APP) proteolytic process. Accordingly, in this example, derivatives with base structure of 1,2,3,4-tetrahydroisoquinoline as well as with chemical structure of cyclopropylmethyl group, and carbamoyl moiety were subjected to determine whether they could modulate significantly ERK-related pathway.

1. Cell Culture

Cell line used in this example were same as those described in example 2.

2. Assay for Extracellular Signal-Regulated Kinase (ERK) Activity

The activation of the ERKs was measured by using anti-phospho-ERK1/2 and anti-ERK1/2 antibodies (Cell Signaling Technology). In brief, T-20 cells were grown in six-well plates at $5 \times 10^5$ cells/well and incubated with culture medium at 37° C. for 18 hours, followed by an additional incubation with culture medium containing 1 µg/ml of tetracycline at 37° C. for 18 hours. Before the experiments, we replaced the medium with DMEM containing 0.5% FBS and treated it with the tested compounds (10 µM each). After treatment, reactions were stopped by placing cells on ice and aspirating off the medium. Cells were harvested and lysed in 50 mM Tris-HCl (pH 8.0), 150 mM NaCl, 5 mM EDTA, 1 mM sodium orthovanadate, 1% Triton X-100, and protease- and phosphatase-inhibitor cocktails. Protein concentration was determined by the BCA assay (Pierce). Each cell lysate, which contained 50 µg proteins, was separated on 12% SDS-polyacrylamide electrophoresis gels, immunoblotted, and identified using anti-phospho-ERK1/2 or anti-ERK1/2 antibody. In this example, T-20 cell line treated with medium containing 1% DMSO and 1 µg/ml of tetracycline was used as positive control group; T-20 cell line treated with medium containing various compounds (10 µM), 1% DMSO and 1 µg/ml of tetracycline were used as test groups for different compounds.

3. Statistical Analysis

The statistical analysis in this example was same as described in example 2,

TABLE 2

The relative levels of ERK activation of certain tetrahydroisoquinoline derivatives in treated cells compared with non-treated cells

| Compound | Activation of ERK1/2 (p-ERK/ERK, (%) |
|---|---|
| Positive Control | 100 |
| Rasagiline | 131 ± 14 |
| 12a | 131 ± 10 |
| 12c | 155 ± 28* |
| 12d | 138 ± 39 |

Each value represents the mean ± SD of three experiments.
*$P < 0.05$, means significantly different compared with the control.

4. Result

As shown in Table 2, the ability to activate ERK from test group using 7-(1-Piperidinecarbamoyloxy)-N-cyclopropylmethyl-1,2,3,4-tetrahydroisoquinoline) (12c) (10 µM) obtained by substituted with R1=cyclopropylmethyl, and R2=1-piperidinyl relative to the ability of 10 µM rasagiline test group, was 1.2 times better than that from rasagiline test group, where $P<0.05$, indicated a statistically significant difference. On the other hand, 12a and 12d test groups exhibited ERK activation abilities similar to that from rasagiline test group, which demonstrated that 1,2,3,4-tetrahydroisoquinoline derivatives with a structure of formula (I) (wherein R1 and R2 were defined therein) have ability to activate ERK.

Example 6

Analysis of the Effect of 1,2,3,4-tetrahydroisoquinoline Derivatives on the Secretion Extent of sAPPα

It is known that monoamine oxidase B (MAO-B) inhibitor can activate directly or indirectly ERK-related pathway, so as to regulate amyloid precursor protein (APP) proteolytic process, which lead to modulate indirectly the secretion of soluble amyloid precursor protein α (sAPPα), and inhibit indirectly the production of insoluble β amyloid-peptides (Aβ). In example 5, it was demonstrated that 1,2,3,4-tetrahydroisoquinoline derivatives 12a, c and d had abilities to activate ERK. Thus, in this example, assay was carried out in γ-30 cells to examine the effect of 1,2,3,4-tetrahydroisoquinoline derivatives (12a, c and d) on the secretion of sAPPα.

1. γ-30 Cell Lines and Cell Culture

As described in reference (3) and (6), briefly described below. PS70 Chinese hamster ovary cell (CHO cell) was used to perform a transfection to obtain γ-30 stably transfected cell line, γ-30 stably transfected cell line was used to express then full length amyloid precursor protein (APP) and human PS1, Aph-1α2, and Pen-2 proteins (Human PS, Aph-1α2, and Pen-2). This cell line could be used as the ideal model cell for detecting α-secretase degradation of amyloid precursor protein (APP).

2. Analysis of the Effect of 1,2,3,4-tetrahydroisoquinoline Derivatives on the Secretion of sAPPα

Each group of corresponding cell lysate in example 5 was prepared to identical protein content. Proteins with different molecular weight were separated by means of electrophoresis on SDS-PAGE and Western Blot assay was carried using anti-Aβ1-17 monoclonal antibody (6E10) (purchased from US Chemicom Co.). In this example, γ-30 cell line treated with medium containing 1% DMSO was used as negative control group, γ-30 cell lines treated with medium containing different compounds (10 μM), 1% DMSO and 1 μg/ml of tetracycline were used as test group for different compounds, respectively.

3. Statistical Analysis

The statistical analysis in this example was same as described in example 2.

Figure 4A:
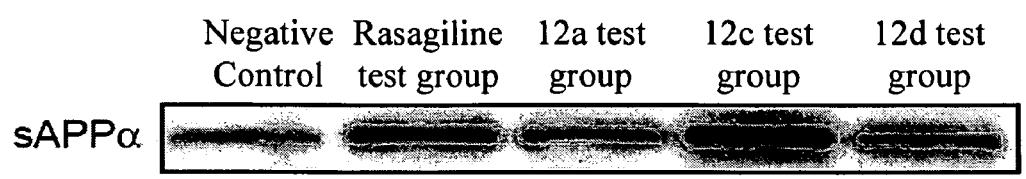
FIG. 4A gives results from the Western blot assay, showing the effect of 1,2,3,4-tetrahydroisoquinoline derivatives on the secretion of soluble amyloid precursor protein α (sAPPα) according to example 4.
Figure 4B:
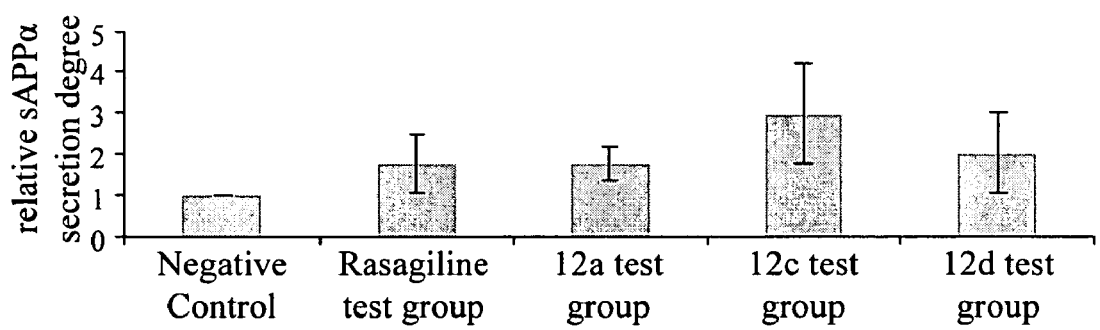
FIG. 4B gives the results of relative sAPPα secretion degree analysis, showing the effect of 1,2,3,4-tetrahydroisoquinoline derivatives on the secretion of soluble amyloid precursor protein α (sAPPα) according to example 4.

4. Result

γ-30 stably transfected cell line expresses full length amyloid precursor protein (APP) and human PS1, Aph-1α2, and Pen-2 proteins. When α-secretase cleavages amyloid precursor protein (APP), soluble amyloid precursor protein α (sAPPα) is formed, which can be used to detect whether a compound has an effect on the secretion of soluble amyloid precursor protein α (sAPPα). To this end, Western blot assay using Aβ1-17 monoclonal antibody (6E10) was carried out to detect soluble amyloid precursor protein α (sAPPα). From the result shown in FIG. 4A, it could be found that protein contents of soluble amyloid precursor protein α (sAPPα) detectable by 1,2,3,4-tetrahydroisoquinoline derivatives (12a, c and d test groups) were higher than that of negative control group, wherein 12c test group corresponded to rasagiline test group and soluble amyloid precursor protein α (sAPPα) detected by 12c test group was better. Thereafter, results from Western blot assay were subjected to quantitatively statistical analysis. From FIG. 4B, it could be found that 1,2,3,4-tetrahydroisoquinoline derivatives (12a, c and d test groups) could promote the secretion of soluble amyloid precursor protein α, wherein 12c test group exhibited better promotion effect than rasagiline test group. Accordingly, it could be proved that 1,2,3,4-tetrahydroisoquinoline derivatives with structure of formula (I) (wherein R1 and R2 were defined therein) could be used to promote the secretion of soluble amyloid precursor protein α (sAPPα).

The invention provides a type of novel 1,2,3,4-tetrahydroisoquinoline derivatives, and in particular, 1,2,3,4-tetrahydroisoquinoline derivatives useful for treating Alzheimer's disease. Said derivatives could be used to inhibit the activity of γ-secretase, reduce the production of β amyloid-peptides (Aβ), activate ERK pathway as well as promote further the formation of sAPPα. As such, a potential neuroprotective activity could be presented and hence may be used as a pathological mechanism to treat Alzheimer's disease.

The novel 1,2,3,4-tetrahydroisoquinoline derivatives provided according to the invention exhibits following advantages over the above-cited prior art and other conventional techniques:

The novel inventive 1,2,3,4-tetrahydroisoquinoline derivatives, because of having structure of formula (I) (wherein R1 and R2 are defined therein) are demonstrated via test that they can inhibit the activity of γ-secretase, and suppresses further the formation of Aβ, so that they can be used to treat Alzheimer's disease.

The novel inventive 1,2,3,4-tetrahydroisoquinoline derivatives, because of having structure of formula (I) (wherein R1 and R2 are defined therein) are demonstrated via test that, relative to known monoamine oxidase B (MAO-B) inhibitors, have better abilities to activate ERK and to promote the secretion of sAPPα, so that they can be used Alzheimer's disease.

The novel inventive 1,2,3,4-tetrahydroisoquinoline derivatives, because of having structure of formula (I) (wherein R1 and R2 are defined therein) are demonstrated via test that they can, at the same time, inhibit the activity of γ-secretase, suppress the formation of Aβ, activate ERK pathway and further promote the secretion of sAPPα, so that they can be used to treat Alzheimer's disease.

The foregoing detailed description is used to illustrate possible embodiments according to the invention without intention to limit the scope of the invention thereto. Equivalent embodiments and variations without departing from the spirit of the invention are intended to fall within the scope of the appended claims.

In summary, the application not only has exact innovation in the method, but also exhibits many above-described advantages over prior art, that is, the invention satisfies fully novelty and non-obviousness required by the legal invention patent criteria.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A type of novel 1,2,3,4-tetrahydroisoquinoline compound with a structure of formula (I):

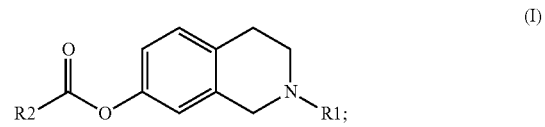

wherein:
R1 represents a structure of formula (II):

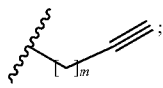
(II)

where m is 1-4;
or R1 represents a structure of formula (III):

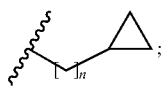
(III)

where n is 1-4;
and wherein:
R2 represents a structure of formula (IV):

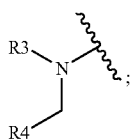
(IV)

wherein R3 is selected from methyl (—CH$_3$), ethyl (CH$_2$CH$_3$) or propyl (—(CH$_2$)$_2$CH$_3$);
wherein R4 is selected from methyl (—CH$_3$), ethyl (CH$_2$CH$_3$) or propyl (—(CH$_2$)$_2$CH$_3$);
or R2 represents a structure of formula (V):

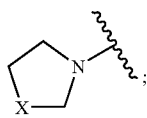
(V)

wherein X is selected from —CH$_2$—, oxygen or sulfur;
or R2 represents a structure of formula (VI):

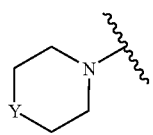
(VI)

wherein Y is selected from —CH$_2$—, oxygen or sulfur.

2. The compound as recited in claim 1, wherein R1 represents a structure of formula (II), where m is 1, and R2 represents a structure of formula (IV); R3 and R4 are methyl (—CH$_3$).

3. The compound as recited in claim 2, wherein said compound is 7-(N-Methyl-N-ethylcarbamoyloxy)-N-propargyl-1,2,3,4-tetrahydroisoquinoline, with R1=propargyl, and R2=N-ethyl-N-methylamino.

4. The compound as recited in claim 1, wherein R1 represents a structure of formula (II), m is 1, and R2 represents a structure of formula (V), wherein X is —CH$_2$—.

5. The compound as recited in claim 4, wherein said compound is 7-(1-Pyrrolidinecarbamoyloxy)-N-propargyl-1,2,3,4-tetrahydroisoquinoline, with R1=propargyl, and R2=1-Pyrrolidyl.

6. The compound as recited in claim 1, wherein R1 represents a structure of formula (II), m is 1, and R2 represents a structure of formula (VI), wherein Y is —CH$_2$—.

7. The compound as recited in claim 6, wherein said compound is 7-(1-Piperidinecarbamoyloxy)-N-propargyl-1,2,3,4-tetrahydroisoquinoline, with R1=propargyl, and R2=1-Piperidinyl.

8. The compound as recited in claim 1, wherein R1 represents a structure of formula (II), m is 1, and R2 represents a structure of formula (VI), wherein Y is oxygen.

9. The compound as recited in claim 8, wherein said compound is 7-(1-Morpholinecarbamoyloxy)-N-propargyl-1,2,3,4-tetrahydroisoquinoline with R1=propargyl, and R2=1-Morpholinyl.

10. The compound as recited in claim 1, wherein R1 represents a structure of formula (III), n is 1, and R2 represents a structure of formula (IV), wherein R3 and R4 are methyl (—CH$_3$).

11. The compound as recited in claim 10, wherein said compound is 7-(N-Methyl-N-ethylcarbamoyloxy)-N-cyclopropylmethyl-1,2,3,4-tetrahydroisoquinoline with R1=cyclopropylmethyl, and R2=N-ethyl-N-methylamino.

12. The compound as recited in claim 1, wherein R1 represents a structure of formula (III), n is 1, and R2 represents a structure of formula (V), wherein X is —CH$_2$—.

13. The compound as recited in claim 12, wherein said compound is 7-(1-Pyrrolidinecarbamoyloxy)-N-cyclopropylmethyl-1,2,3,4-tetrahydroisoquinoline with R1=cyclopropylmethyl, and R2=1-Pyrrolidyl.

14. The compound as recited in claim 1, wherein R1 represents a structure of formula (III), n is 1, and R2 represents a structure of formula (VI), wherein Y is —CH$_2$—.

15. The compound as recited in claim 14, wherein said compound is 7-(1-Piperidinecarbamoyloxy)-N-cyclopropylmethyl-1,2,3,4-tetrahydroisoquinoline with R1=cyclopropylmethyl, and R2=1-Piperidinyl.

16. The compound as recited in claim 1, wherein R1 represents a structure of formula (III), n is 1, and R2 represents a structure of formula (VI), wherein Y is oxygen.

17. The compound as recited in claim 16, wherein said compound is 7-(1-Morpholinecarbamoyloxy)-N-cyclopropylmethyl-1,2,3,4-tetrahydroisoquinoline with R1=cyclopropylmethyl, and R2=1-Morpholinyl.

18. A process for preparing the compound the recited in claim 1, said process comprising:
reacting 1,2,3,4-tetrahydroisoquinoline with trifluoroaceticanhydride (CF$_3$CO)$_2$O) and potassium hydroxide (KOH), to form N-Trifluoroacetyl-1,2,3,4-tetrahydroisoquinoline;
reacting N-Trifluoroacetyl-1,2,3,4-tetrahydroisoquinoline with chloroacetyl chloride and aluminum chloride (AlCl$_3$), to form 7-Chloroacetyl-N-trifluoroacetyl-1,2,3,4-tetrahydroisoquinoline;
reacting 7-Chloroacetyl-N-trifluoroacetyl-1,2,3,4-tetrahydroisoquinoline with 3-chloroperoxybenzoic acid (mCPBA), to form 7-Chloroacetoxy-N-trifluoroacetyl-1,2,3,4-tetrahydroisoquinoline;
reacting 7-Chloroacetoxy-N-trifluoroacetyl-1,2,3,4-tetrahydroisoquinoline with sodium thiomethoxide (NaSCH$_3$), to form 7-Hydroxy-1,2,3,4-tetrahydroisoquinoline hydrochloride salt;
reacting 7-Hydroxy-1,2,3,4-tetrahydroisoquinoline hydrochloride salt with propargyl bromide or bromomethyl cyclopropane, respectively, and potassium carbonate ($K_2CO_3$), to form 7-Hydroxy-N-propargyl-1,2,3,4-tetrahydroisoquinoline or 7-Hydroxy-N-cyclopropylmethyl-1,2,3,4-tetrahydroisoquinoline; and reacting respectively 7-Hydroxy-N-propargyl-1,2,3,4-tetrahydroisoquinoline or 7-Hydroxy-N-cyclopropylmethyl-1,2,3,4-tetrahydroisoquinoline, with R2-CO—Cl, and sodium hydride (NaH), wherein R2 represents N-ethyl-N-methylamino, 1-Pyrrolidyl, 1-Piperidinyl or 1-Morpholinyl, to obtain said 1,2,3,4-tetrahydroisoquinoline compound with a structure of formula (I).

19. A pharmaceutical composition, comprising the 1,2,3,4-tetrahydroisoquinoline compound as recited in claim 1 or pharmacologically acceptable salt form thereof, in admixture with suitable pharmaceutically acceptable excipient or carrier.

20. A pharmaceutical composition as recited in claim 19, useful for inhibiting the activity of γ-secretase.

21. A pharmaceutical composition as recited in claim 19, useful for activating extracellular signal-regulated protein kinase (ERK) pathway, and further promoting the secretion of soluble amyloid precursor protein α.

22. A pharmaceutical composition as recited in claim 19, useful for inhibiting the activity of γ-secretase, and activating extracellular signal-regulated protein kinase (ERK) pathway, and further promoting the secretion of soluble amyloid precursor protein α, concurrently.

23. A pharmaceutical composition as recited in claim 19, useful for treating diseases that involve nerve cell necrosis caused by the increase of insoluble β amyloid-peptides, resulting in loss of memory and learning function, dementia and diseases with impaired cognitive process.

24. A pharmaceutical composition as recited in claim 23, wherein said diseases with impaired cognitive process are Alzheimer's disease or other dementia, or Parkinson's disease.

25. A pharmaceutical composition as recited in claim 19, wherein said excipient is selected from the group consisting of diluent, filler, binder, disintegrating agent, and lubricant.

26. A pharmaceutical composition as recited in claim 19, wherein said excipient is selected from the group consisting of microcrystalline cellulose, polyvinylpyrrolidone (PVP), corn starch, modified starches, sodium carboxymethylstarch (sodium starch glycolate), resin, gelatinized starches, sugars, polyethylene glycol (PEG), polyvinyl alcohol, hydroxypropyl cellulose, methyl cellulose, hydroxymethyl cellulose, and hydroxypropyl methyl cellulose.

\* \* \* \* \*